(12) United States Patent
Omura et al.

(10) Patent No.: US 7,400,079 B2
(45) Date of Patent: Jul. 15, 2008

(54) ULTRASONIC PROBE

(75) Inventors: Masayoshi Omura, Saitama (JP); Tohru Mizuguchi, Yamanashi (JP); Koumei Hatano, Fuchu (JP)

(73) Assignees: Olympus Corporation, Tokyo (JP); GSK Corporation, Tokyo (JP)

( * ) Notice: Subject to any disclaimer, the term of this patent is extended or adjusted under 35 U.S.C. 154(b) by 569 days.

(21) Appl. No.: 10/737,277

(22) Filed: Dec. 16, 2003

(65) Prior Publication Data

US 2004/0215079 A1    Oct. 28, 2004

(30) Foreign Application Priority Data

Dec. 19, 2002  (JP) .............................. 2002-368893

(51) Int. Cl.
*H01L 41/053* (2006.01)
*H01L 41/083* (2006.01)

(52) U.S. Cl. .................... 310/355; 310/327; 310/335

(58) Field of Classification Search ................. 310/327, 310/334, 335; 600/459
See application file for complete search history.

(56) References Cited

U.S. PATENT DOCUMENTS

| | | | | |
|---|---|---|---|---|
| 4,281,550 A | * | 8/1981 | Erikson ........................ | 73/626 |
| 5,176,140 A | * | 1/1993 | Kami et al. .................. | 600/459 |
| 5,317,229 A | * | 5/1994 | Koehler et al. .............. | 310/334 |
| 5,722,644 A | * | 3/1998 | Kinoshita et al. ........... | 267/141 |
| 5,766,703 A | | 6/1998 | Mori et al. | |
| 5,884,627 A | | 3/1999 | Wakabayashi et al. | |
| 6,307,302 B1 | * | 10/2001 | Toda .......................... | 310/334 |
| 6,599,640 B2 | * | 7/2003 | Suzuki et al. ............. | 428/476.3 |
| 6,781,287 B1 | * | 8/2004 | Dam et al. .................. | 310/334 |

FOREIGN PATENT DOCUMENTS

| | | |
|---|---|---|
| EP | 0 589 396 A2 | 3/1994 |
| JP | 11-252695 | 9/1999 |
| JP | 2000-054274 | 2/2000 |
| JP | 2000-165995 | 6/2000 |

* cited by examiner

*Primary Examiner*—Darren Schuberg
*Assistant Examiner*—Derek J Rosenau
(74) *Attorney, Agent, or Firm*—Scully, Scott, Murphy & Presser, P.C.

(57) ABSTRACT

An ultrasonic probe includes an ultrasonic transducer which is formed by sequentially laminating an acoustic lens, an acoustic matching layer, a piezoelectric element, and a backing member. The backing member arranged on a surface opposed side of the acoustic matching layer and the acoustic lens arranged to the piezoelectric element contains a synthetic rubber containing a mixture including acrylonitrile-butadiene rubber (NBR), ethylen-propylene terpolymer (EPDM), and at least inorganic fine powders.

3 Claims, 2 Drawing Sheets

ULTRASONIC PROBE

This application claims benefit of Japanese Application No. 2002-368893 filed on Dec. 19, 2002, the contents of which are incorporated by this reference.

BACKGROUND OF THE INVENTION

1. Field of the Invention

The present invention relates to an ultrasonic transducer which is used in the body cavity and is preferable to ultrasonic diagnosis and the like.

2. Description of the Related Art

A mechanical scanning ultrasonic endoscope is used for the spectrographic diagnosis of the luminal surface organ and the ultrasonic diagnosis of the peripheral organ and the tissue by inserting a dedicated scope into the digestive tract such as the esophagus, the stomach, the duodenum, and the large intestine or the urinary tract such as the urethra, bladder, and the ureter. An ultrasonic transducer for transmitting and receiving ultrasonic waves is attached to the distal end portion of the mechanical scanning ultrasonic endoscope.

The ultrasonic transducer of the mechanical scanning ultrasonic endoscope is covered with an exterior cap containing a resin member for ultrasonic transmission. The exterior cap is filled with an acoustic medium. The acoustic medium efficiently propagates, through the living body, the ultrasonic waves generated by the ultrasonic transducer. The acoustic medium contains, as a general material, insulating oil such as liquid paraffin and butanediol.

However, the insulating oil has a high acoustic-attenuating rate. As a consequence, the ultrasonic endoscope with a high frequency capable of providing an image with a high resolution has such a problem that an ultrasonic signal is attenuated in the acoustic medium and thus a preferable image is not obtained.

In order to prevent the occurrence of the problem, the acoustic medium contains water that displays a low acoustic-attenuation, or an aqueous solution obtained by adding an additive to water (hereinafter, simply referred to as an aqueous solution).

The aqueous solution exposes the ultrasonic transducer for a long time and then the property of the ultrasonic transducer gradually deteriorates. Therefore, in order to prevent the deterioration in property of the ultrasonic transducer, the aqueous solution is injected every ultrasonic endoscope examination and the aqueous solution is removed after finishing the examination.

However, with the ultrasonic endoscope inserted into the body cavity, the injection and removal of the aqueous solution after/before the examination becomes a complicated work for an operator in view of the configuration of the ultrasonic endoscope.

Then, in the ultrasonic endoscope having the ultrasonic transducer with the high-frequency property, the ultrasonic transducer is subjected to thin-film coating (hereinafter, waterproof coating) using high water-resisting resin.

SUMMARY OF THE INVENTION

According to the present invention, an ultrasonic probe includes an ultrasonic transducer which is formed by sequentially laminating an acoustic lens, an acoustic matching layer, a piezoelectric element, and a backing member. The backing member which is arranged to the piezoelectric element on the surface opposed to the acoustic matching layer and the acoustic lens is a synthetic rubber for attenuating the ultrasonic waves, containing acrylonitrile-butadiene rubber (NBR), ethylen-propylene terpolymer (EPDM), and a mixture including at least inorganic fine powders.

The above and other objects, features and advantages of the invention will be become more clearly understood from the following description referring to the accompanying drawings.

DESCRIPTION OF THE PREFERRED EMBODIMENTS

Hereinbelow, a description is given of an embodiment of the present invention with reference to the drawings.

Figure 1:
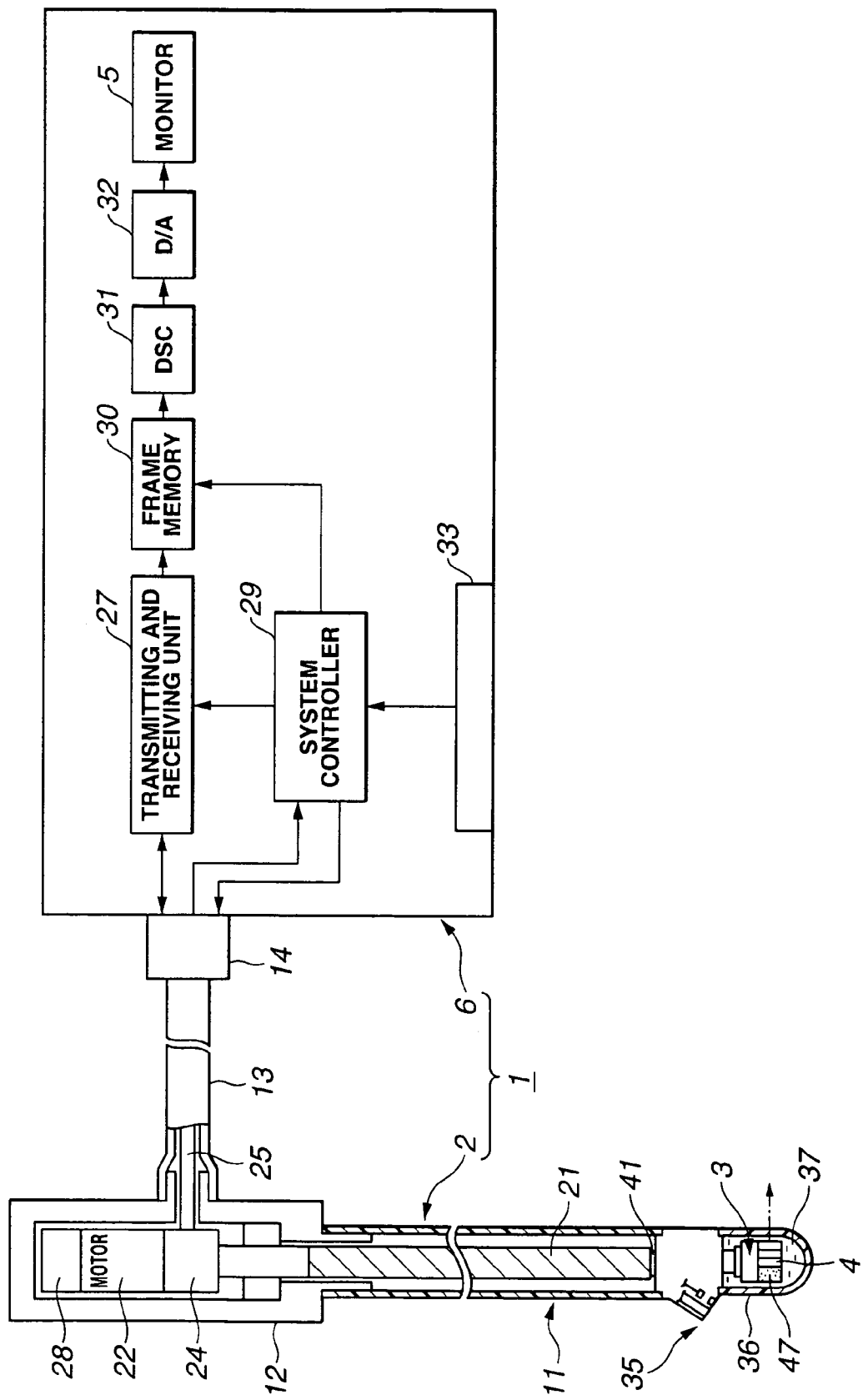
FIG. 1 is a diagram for explaining the entire configuration of an ultrasonic diagnostic apparatus.

Referring to FIG. 1, an ultrasonic diagnostic system 1 mainly comprises an ultrasonic endoscope 2 and an ultrasonic observing apparatus 6. The ultrasonic endoscope 2 has, for example, an ultrasonic probe and optical observing means and is detachably connected to the ultrasonic observing apparatus 6.

The distal end portion of an inserting portion in the ultrasonic endoscope 2 has a piezoelectric element (refer to FIG. 2) 4 forming an ultrasonic transducer 3 for transmitting and receiving ultrasonic waves to/from a subject.

The ultrasonic observing apparatus 6 performs the signal processing for the piezoelectric element 4, and generates an image signal for displaying an ultrasonic tomographic image (B mode image) to a monitor 5.

The ultrasonic endoscope 2 has an elongated flexible inserting portion 11 which is inserted in the body cavity. An operating portion 12 is arranged at the proximal end of the inserting portion 11. A cable portion 13 is extended from the operating portion 12. A connector 14 is arranged at an end portion of the cable portion 13. The connector 14 is detachably connected to the ultrasonic observing apparatus 6.

A flexible shaft 21 is inserted in the inserting portion 11 of the ultrasonic endoscope 2. The ultrasonic transducer 3 is attached to the distal end of the flexible shaft 21 via a hard shaft 41. The proximal end of the flexible shaft 21 is connected to a motor 22 arranged in the operating portion 12.

By rotating the motor 22, the flexible shaft 21 and the ultrasonic transducer 3 are rotated. Thus, ultrasonic waves transmitted from the piezoelectric element 4 forming the ultrasonic transducer 3 are mechanically radial-scanned.

Figure 2:
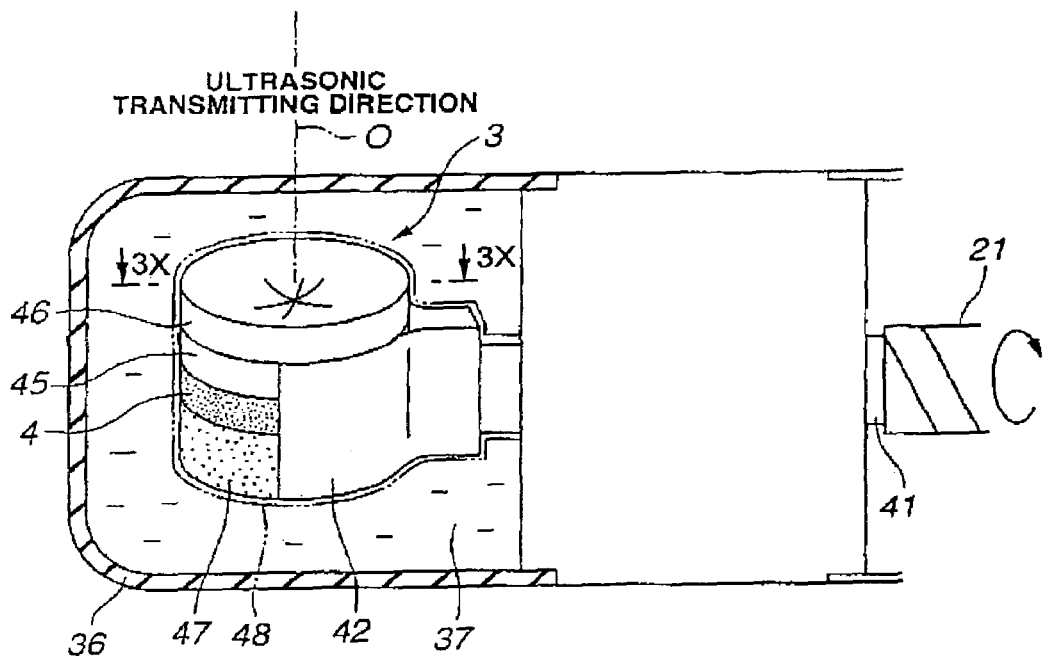
FIG. 2 is a diagram showing the configuration of an ultrasonic transducer arranged on the distal end side of an ultrasonic endoscope.
Figure 3:
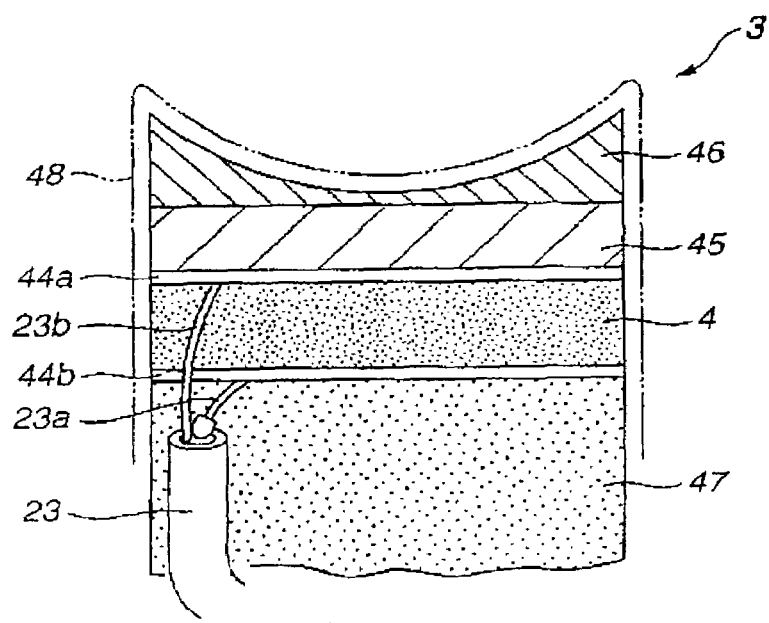
FIG. 3 is a cross-sectional view of transducer 3 as bisected by a line 3X-3X as shown in FIG. 2.

Referring to FIG. 3, which provides a cross-sectional view of transducer 3 as bisected by a line identified as 3X-3X in FIG. 2, a coaxial cable 23 is shown connected to the piezoelectric element 4 in the ultrasonic transducer 3. The coaxial cable 23 is inserted in a hollow portion of the flexible shaft 21, and is connected to a slip ring 24 arranged in the operating portion 12. A cable 25 connected to the contact on a stator side of the slip ring 24 is connected to a transmitting and receiving portion 27 for transmitting and receiving the signal in the ultrasonic observing apparatus 6.

A rotary encoder 28 for detecting the motor 22 and a rotating angle of the motor 22 is connected to a system controller 29 in the ultrasonic observing apparatus 6 via the cable 25.

The system controller 29 controls the rotation of the motor 22 and controls the transmission and reception of ultrasonic waves. The transmitting and receiving portion 27 applies a driving signal to the piezoelectric element 4 in the ultrasonic transducer 3, thereby transmitting the ultrasonic waves. A signal transmitted from the piezoelectric element 4 and reflected by the subject is received by the piezoelectric element 4 and is converted into an echo signal. The echo signal is amplified and is then converted into the digital signal by an A/D converter (not shown) and is stored in a temporary frame memory 30 under the control of the system controller 29. An input device 33 is connected to the system controller 29 in order to provide system users with an interface with which to enter system control commands and instructions during operation. Input device 33 may comprise any known user input device such as a trackball, mouse, keyboard. etc.

Echo signal data stored in the frame memory 30 is raster data in the radial direction, is converted into data of the orthogonal coordinate system by a digital scan converter (hereinafter, abbreviated to a DSC) 31, and is output to the monitor 5 via the D/A converter 32. Consequently, the B mode image is displayed on a screen of the monitor 5.

An exterior cap 36 for covering the ultrasonic transducer 3 is fixed to a distal end portion 35 of the inserting portion 11. The exterior cap 36 is filled with an acoustic medium 37 such as an aqueous solution for transmitting the ultrasonic waves with low attenuation.

The distal end portion 35 has an optical illuminating window and an optical observing window, thus to form optical observing means for endoscope examination.

Next, the configuration of the ultrasonic transducer 3 will be described with reference to FIGS. 2 and 3.

The ultrasonic transducer 3 is connected and fixed to a holder 42. Referring to FIGS. 2 and 3, the ultrasonic transducer 3 mainly comprises the piezoelectric element 4, an acoustic matching layer 45, an acoustic lens 46, and a backing member 47.

The piezoelectric element 4 is disc-shaped. Electrodes 44a and 44b are respectively provided on the piezoelectric element 4 at one side and the other side of the surfaces thereof. For the purpose of clarifying the electrodes 44a and 44b with reference to FIG. 3, the electrodes 44a and 44b are referred to as an upper electrode 44a and a lower electrode 44b, respectively.

The acoustic matching layer 45 is disc-shaped and is arranged onto the surface of the piezoelectric element 4 in the ultrasonic transmitting direction. The ultrasonic transmitting direction is indicated by reference numeral 0 in FIG. 2. The surface of the piezoelectric element 4 in the ultrasonic transmitting direction is referred to as a front surface or upper surface and, further, is functionally referred to as an ultrasonic transmitting and receiving surface.

When expressing, by λ, the wavelength of the center frequency of the ultrasonic wave generated in the piezoelectric element 4, the thickness dimension of the acoustic matching-layer 45 is ¼ of λ, i.e., λ/4. The acoustic matching layer 45 is made of a material having a value between the acoustic impedance of the piezoelectric element 4 and the acoustic impedance of the acoustic medium 37.

The acoustic lens 46 is optically plane-concave-shaped, and is arranged onto the upper surface of the acoustic matching layer 45. The acoustic lens 46 converges the ultrasonic waves transmitted from the piezoelectric element 4.

The backing member 47 is arranged to the rear surface opposed to the side in the ultrasonic transmitting direction 0 of the piezoelectric element 4. The backing member 47 attenuates the ultrasonic waves.

A ground line 23b and a signal line 23a of the coaxial cable 23 are connected to the upper electrode 44a and lower electrode 44b, respectively.

Referring to FIGS. 2 and 3, the surface of the ultrasonic transducer 3 arranged in the exterior cap 36 is protected by the holder 42 and a surface coating film 48 such as parylene.

At least an opposed portion of the exterior cap 36 to the ultrasonic transducer 3 is made of a material through which the ultrasonic waves transmit, such as a polyethylene resin member, and forms an acoustic window for transmitting and receiving the ultrasonic waves.

According to the embodiment, the backing member 47 arranged to the rear surface side as the opposed surface of the ultrasonic transmitting and receiving surface of the piezoelectric element 4 contains a synthetic rubber which mainly having acrylonitrile-butadiene rubber (NBR), ethylen-propylene terpolymer (EPDM), and further mixes at least a filling agent of inorganic fine powders such as metallic powders and glass powders.

By varying the amount of the filling agent, the hardness, ultrasonic absorbing coefficient-, and acoustic impedance of the backing member 47 has equivalent to the hardness (JIS-AHS) of 94, ultrasonic absorbing coefficient of 15 [dB/mm] at 5 MHz, and acoustic impedance of $5.7 \times 10^6$ [Kg/(m$^2$·s)] in a conventional backing member containing ferrite, respectively.

In this case, the backing member 47 is a mixture which basically contains acrylonitrile-butadiene rubber (NBR) and ethylen-propylene terpolymer (EPDM) and which mixes at least a filling agent containing inorganic fine powders such as metallic powders and glass powders. In the configuration, as compared with the conventional art, the synthetic rubber having the hardness of 80 to 100 degrees (JIS-AHS) at the A scale in conformity with the JISK6253 and the ultrasonic absorbing coefficient of 10 (dB/mm) or more at 5 MHz is used as the backing member 47 and then it has a higher mechanical strength. Further, the waterproof capability is improved and in the case of using the backing member 47 in the acoustic member 37 containing the aqueous solution with the low attenuation, the aging deterioration in ultrasonic property such as the sensitivity and the spectrum is minimized. That is, the ultrasonic transducer 3 is realized with the stable property.

When the backing member 47 has the percentage of absorption of 2.5% or less (in conformity with JISK6258 and JISK7209) and the acoustic impedance of $1 \times 10^6$ to $8 \times 10^6$ [kg/(m$^2$·s)] as the property, the deterioration in ultrasonic property such as the sensitivity and the spectrum is minimized.

Various methods for measuring the percentage of absorption are examined. For example, in the experiment system prescribed by JIS7209, the percentage of absorption of plastic is a mass change of the subject after immersing the subject in water under a constant time-condition and a constant temperature condition.

The percentage of absorption of synthetic rubber forming the backing member in the ultrasonic transducer is measured basically in conformity with the JISK6258 and is a mass change of the subject after immersing the subject in water.

According to the embodiment, the experiment system is set in view of the actual using environment as follows.

That is, the subject (also described as a test piece) is a plate member with the shape of 20 mm×20 mm and the thickness of 1.5 to 2 mm, and a mass M0 is instrumented by using a precision electronic force balance. Then, the test piece is immersed in the water with the depth of 15 mm to 20 mm, and is placed in a thermostatic chamber with the ambient temperature of 55±2° C. for 48±1 hours.

After a predetermined time, the test piece is taken out from the thermostatic chamber, and is left in air drying for 15 to 30 minutes. A mass M1 of the test piece is instrumented by using the precision electronic force balance.

Then, the percentage of absorption is calculated by a formula of (M1−M0)/M0 with the above-instrumented value.

Tungsten maybe used as the metallic powders of the filling agent. As recent ultrasonic diagnostic application, the ultrasonic examination during the operation is used for an open gantry MRI (nuclear magnetic resonance imaging) apparatus. An ultrasonic transducer for the open gantry MRI apparatus is developed. The backing member mounted on the ultrasonic transducer is filled with magnetic powders such as ferrite and thus may generate image artifacts in MRI images taken, which artifacts could impede a user's ability to use the MRI image for diagnostic support. Therefore, in this case, in order to prevent the influence on the MRI image, the filling agent forming the backing member 47 in the ultrasonic transducer 3 may contain metallic oxides such as non-magnetic and non-conductive tungsten oxides.

As mentioned above, the ultrasonic probe in the ultrasonic endoscope 2 mainly comprises the ultrasonic transducer 3, the exterior cap 36, the acoustic medium 37, the cable portion 13, and the connector 14.

Next, the operation will be described according to the embodiment.

The inserting portion 11 of the ultrasonic endoscope 2 shown in FIG. 1 is inserted into the living body. Further, when the acoustic examination is necessary in addition to the optical examination using the observing means arranged to the distal end portion 35, the exterior cap 36 is touched to the surface of the portion to be examined.

Next, a pulse transmitting signal from the transmitting and receiving unit 27 is applied to the piezoelectric element 4 of the ultrasonic transducer 3, the ultrasonic waves are excited by the piezoelectric element 4 and are converged to the acoustic lens 46, and the ultrasonic waves are transmitted.

The ultrasonic waves are propagated through the acoustic medium 37, are transmitted to an acoustic window portion in the exterior cap 36 opposed to the piezoelectric 4, and are output to the living body side touching the acoustic window portion.

The acoustic impedance of the living body is approximately $1.5 \times 10^6$ [kg/(m$^2$·s)]. The acoustic impedance of the acoustic window portion is approximate to that of the living body and therefore reflecting waves of the ultrasonic waves are reduced on the contact surface between the outer surface and the living body.

The ultrasonic waves transmitted to the living body side are reflected by a portion at which the acoustic impedance changes on the living body side. The reflected ultrasonic waves trace a route inverse to that for transmission. That is, the ultrasonic waves are received by the piezoelectric element 4, are converted into an electric signal, i.e., an echo signal, are detected and amplified by the transmitting and receiving unit 27, thereafter, are A/D converted, and are sequentially stored in the frame memory 30 as raster data of the ultrasonic data.

The raster data is converted into the raster data of the orthogonal coordinate system by the DSC 31, is converted into an analog video signal by the D/A converter 32, and is output to the monitor 5 together with a synchronous signal (not shown). Consequently, the B mode image is displayed on the screen of the monitor 5.

According to the embodiment, the exterior cap 36 at the distal end portion of the ultrasonic endoscope 2 is filled with the acoustic medium 37 such as water, and the ultrasonic transducer 3 is immersed in the acoustic medium 37. The backing member 47 for attenuating the ultrasonic waves contains material that is preferably waterproof and displays a high ultrasonic absorbing coefficient on the rear surface of the opposed surface of the ultrasonic transmitting and receiving surface of the piezoelectric element 4, which element generates the ultrasonic waves in the ultrasonic transducer 3. Therefore, the aging change is minimized, that is, the aging deterioration in ultrasonic property is minimized as compared with the conventional art.

Next, a result is given of the test of the percentage of absorption in conformity with the JISK7209 (the mass change after immersing in the distilled water of 55° C. for 48 hours) with the backing member 47 according to the embodiment and with the conventional backing member having ferrite for comparison in the following table.

| BACKING MEMBER | PERCENTAGE OF ABSORPTION | ACOUSTIC IMPEDANCE [kg/(m$^2$·s)] | ULTRASONIC ABSORBING COEFFICIENT [dB/mm](5 MHz) |
|---|---|---|---|
| (Immersion in distilled water of 55° C. for 48 hours) | | | |
| BACKING MEMBER ACCORDING TO THE EMBODIMENT | 0.5% | $5.7 \times 10^6$ | 17.2 |
| BACKING MEMBER CONTAINING FERRITE | 4.9% | $5.7 \times 10^6$ | 15.0 |

As indicated in the table, in the ultrasonic transducer 3 using the backing member 47 as a main portion according to the embodiment, the water proof property is excessively improved and the aging deterioration in ultrasonic property is minimized, as compared with that of the conventional ultrasonic transducer using the backing member having the ferrite.

The acoustic impedance is reduced to $1 \times 10^6$ [kg/(m$^2$·s)] by decreasing the filling agent.

Further, the ultrasonic transducer with high sensitivity is formed by optimizing the acoustic matching layer and the backing member 47 with low acoustic impedance.

According to the present invention, the acoustic medium is not limited to the aqueous solution with the low attenuation for the ultrasonic waves and can be oil with the low attenuation for the ultrasonic waves.

Having described the preferred embodiments of the invention referring to the accompanying drawings, it should be understood that the present invention is not limited to those precise embodiment and various changes and modifications thereof could be made by one skilled in the art without departing from the spirit or scope of the invention as defined in the appended claims.

What is claimed is:

1. An ultrasonic probe for an endoscope comprising an ultrasonic transducer, the ultrasonic transducer comprising, by sequential lamination:
   an acoustic lens;
   an acoustic matching layer;
   a piezoelectric element;
   a backing member that attenuates ultrasonic waves and comprises a synthetic rubber having a mixture including acrylonitrile-butadiene rubber (NBR), ethylene-propylene terpolymer (EPDM), and at least inorganic fine powders, and displays: 1) a hardness property of between 80 and 100 degrees in an A scale in conformity with JISK6253, and 2) an ultrasonic absorbing coefficient of 10 [dB/mm] or more at a frequency of 5 MHz; and an exterior cap sealably covers the ultrasonic transducer and contains an acoustic medium comprising an aqueous solution that immerses the ultrasonic transducer and imposes a low attenuation on ultrasonic waves arriving at a surface of the ultrasonic transducer, which aqueous solution is obtained by adding an additive to the water, or oil that displays a low attenuation to ultrasonic waves, wherein upon immersion of the ultrasonic transducer in the aqueous solution, the backing member displays: 1) a percentage of absorption that is 2.5% or less and 2) an acoustic impedance that is within a range of $1\times10^6$ to $8\times10^6$ [kg/(m$^2$·s)].

2. An ultrasonic probe for an endoscope according to claim 1, further comprising:
a flexible shaft which rotates the ultrasonic transducer using a driving motor.

3. An ultrasonic probe for an endoscope according to claim 1, further comprising:
a coating film which covers the ultrasonic transducer to protect it from the acoustic medium.

* * * * *